United States Patent [19]
Jang

[11] Patent Number: 6,051,014
[45] Date of Patent: Apr. 18, 2000

[54] PERCUTANEOUS FILTRATION CATHETER FOR VALVE REPAIR SURGERY AND METHODS OF USE

[75] Inventor: Yue-Teh Jang, Fremont, Calif.

[73] Assignee: Embol-X, Inc., Mountain View, Calif.

[21] Appl. No.: 09/170,359

[22] Filed: Oct. 13, 1998

[51] Int. Cl.$^7$ .......................... A61B 17/00; A61M 29/00
[52] U.S. Cl. .......................... 606/200; 606/191; 604/96
[58] Field of Search ..................... 606/200, 194, 606/191; 604/96

[56] References Cited

U.S. PATENT DOCUMENTS

| | | | |
|---|---|---|---|
| 4,969,891 | 11/1990 | Gewertz | 606/200 |
| 5,133,733 | 7/1992 | Rasmussen et al. | 606/200 |
| 5,147,379 | 9/1992 | Sabbaghian et al. | 606/206 |
| 5,769,816 | 6/1998 | Barbut et al. | 606/220 |
| 5,769,871 | 6/1998 | Kelly et al. | 600/200 |
| 5,876,367 | 3/1999 | Kaganov et al. | 606/200 |
| 5,908,435 | 6/1999 | Samuels | 606/200 |

*Primary Examiner*—Gary Jackson
*Attorney, Agent, or Firm*—Lyon & Lyon LLP

[57] ABSTRACT

A percutaneous filtration catheter used to entrap emboli from a patient's aorta and heart during cardiac surgery. The catheter has an elongate member, a proximal end, and a distal end. A balloon occluder is mounted on the distal end of the elongate member and an expandable filter is mounted on the elongate member distal the balloon occluder. Methods for using the devices are also disclosed herein.

22 Claims, 3 Drawing Sheets

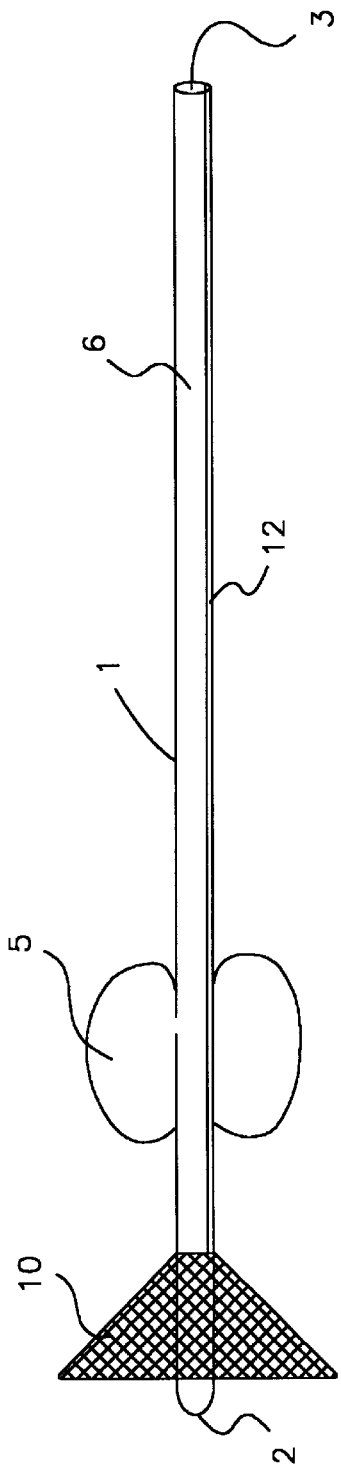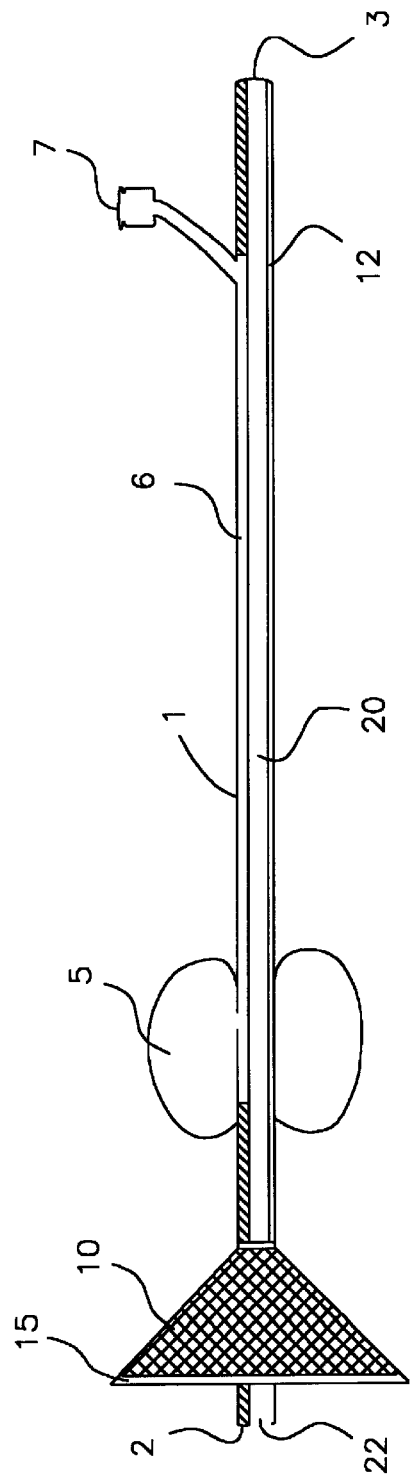

PERCUTANEOUS FILTRATION CATHETER FOR VALVE REPAIR SURGERY AND METHODS OF USE

FIELD OF THE INVENTION

The present invention relates generally to filter devices for placement in a blood vessel to capture embolic material, and more particularly to a catheter system having an associated filter for percutaneous placement in an aorta to entrap embolic material from the aorta and heart during cardiac surgery.

BACKGROUND OF THE INVENTION

Stroke has become a major source of morbidity following coronary artery bypass and other cardiovascular surgeries, including valvular repair, septal defect repair, removal of atrial myxoma, aneurysm repair, and myocardial drilling. Classic factors associated with an increased post-operative stroke rate are advanced age, severe left ventricular dysfunction, long standing diabetes, protracted cardiopulmonary bypass time, severe perioperative hypotension, history of previous stroke, and bilateral carotid disease. Possible mechanisms of perioperative stroke include a reduction in cerebral blood flow through a stenotic extracranial or intracranial vessel, embolization of atherosclerotic debris from an ulcerated carotid artery plaque or aortic plaque, embolization of post-infarction left ventricular mural thrombus or atrial thrombus, and embolization of air inadequately evacuated from the heart or aorta. In valvular repair surgery, manipulation of the heavily calcific aortic or mitral valve may result in calcium dislodgment in the left coronary artery or left ventricle, with subsequent embolization. Although atheromatous debris most frequently embolizes to the brain, other affected body sites include the spleen, kidney, pancreas, and gastrointestinal tract. Embolization of these peripheral organs can lead to tissue ischemia or death.

In addition to stroke, other factors, e.g., chest wall trauma, contributing to morbidity in cardiac surgeries often arise from the use of cardiopulmonary bypass for circulatory support and median sternotomy. Minimally invasive procedures using beating-heart and port-access approach have been developed to achieve aortic occlusion, cardioplegia delivery, and left ventricular decompression to allow coronary revascularization and other cardiac procedures to be performed in a less invasive fashion.

A need therefore exists for less invasive devices and methods which facilitate aortic occlusion and/or cardioplegia delivery in cardiac surgeries and provide an arterial filter for reducing a patient's risk of perioperative stroke.

SUMMARY OF THE INVENTION

The present invention provides a percutaneous filtration catheter having the ability to capture emboli, including atheromatous fragments, fat, myocardial tissue debris, and air. The catheter further includes capabilities to provide aortic occlusion and cardioplegia delivery in cardiac surgeries, especially in heart valve repair.

In one embodiment, the catheter comprises an elongate member having proximal and distal ends. The distal end has (1) a balloon occluder which communicates with a lumen carried by the elongate member, and (2) an expandable filter mounted on the elongate member distal to the balloon occluder. The balloon occluder and the expandable filter are operated independently at the proximal end of the elongate member. The expandable filter typically has a proximal edge bonded circumferentially and continuously to the elongate member, and a distal edge which expands radially outward on activation.

In another embodiment, the elongate member has a second lumen for infusing fluid, such as cardioplegia solution. The expandable filter may comprise an expansion frame, which may have an umbrella frame in one embodiment (for construction, see Barbut et al., U.S. Pat. No. 5,769,816, and Ambrisco et al., U.S. Ser. No. 09/070,660, both incorporated herein by reference in their entirety) and an inflation seal in another embodiment (for construction, see Barbut et al., U.S. Pat. No. 5,769,816). Furthermore, in certain embodiments, the expandable filter is operable by manipulating at least one pull string at the proximal end of the elongate member.

The present invention also provides methods for capturing embolic material in cardiac surgeries, thereby protecting a patient from neurologic complication due to embolization. The methods employ a percutaneous filtration catheter having an elongate member with proximal and distal ends, a balloon occluder mounted on the distal end of the elongate member, and an expandable filter mounted on the elongate member distal the balloon occluder. A percutaneous incision in a patient's peripheral artery, such as a femoral or brachial artery, is made followed by insertion of the elongate member through the incision. In minimally invasive cardiac procedures, the percutaneous filtration catheter can be introduced percutaneously through a peripheral artery, or alternatively, through a minimal access port, often located in a patient's intercostal space, to the ascending aorta. The distal end of the catheter is then advanced into the ascending aorta. The filter is expanded and positioned above the aortic valve to entrap embolic material from flowing downstream to peripheral organs. The balloon occluder is inflated to provide circulatory isolation of the heart and coronary blood vessels from the peripheral vascular system. In the embodiment which includes a second lumen, the second lumen can be used to (1) deliver cardioplegia solution upstream to the heart to arrest cardiac function, or (2) to carry a pressure monitor. After cardiac arrest is achieved and cardiopulmonary bypass is initiated for circulatory support, a variety of cardiothoracic surgeries can then be performed, including coronary artery bypass grafting, heart valve repair, septal defect repair, removal of atrial myxoma, aneurysm repair, and myocardial drilling.

It will be understood that are many advantages to using a percutaneous filtration catheter as disclosed herein. For example, the catheter provides (1) a percutaneous access for catheter insertion, obviating the need for an extensive tissue incision, (2) aortic occlusion through inflating a balloon occluder, thereby minimizing damage to the aortic wall and reducing the risk of emboli dislodgment as compared to traditional clamping, (3) a filter which entraps embolic material during cardiac surgery, thereby reducing a patient's risk of stroke perioperatively, (4) cardioplegia delivery upstream to the heart for cardiac arrest, and (5) access for devices to be introduced through an intercostal incision in minimally invasive cardiac procedures.

BRIEF DESCRIPTION OF THE DRAWINGS

FIG. 1 depicts a percutaneous filtration catheter according a first embodiment.

FIG. 2 depicts a percutaneous filtration catheter according to another embodiment, the catheter having a second lumen.

DETAILED DESCRIPTION

Figure 3:
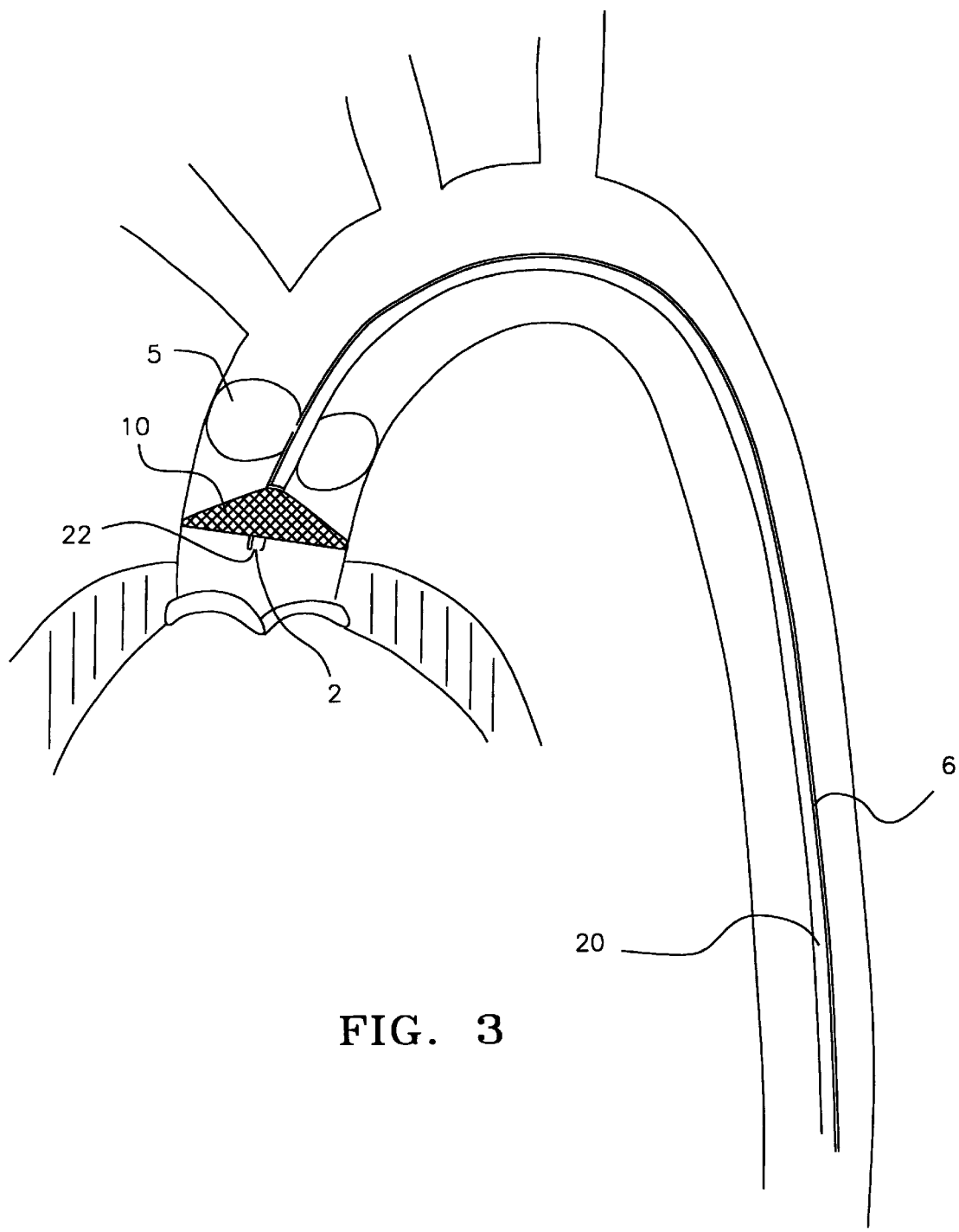
FIG. 3 depicts a percutaneous filtration catheter positioned in an ascending aorta.

The devices and methods disclosed herein can be used in patients who have been identified as being at risk for embolization during cardiothoracic surgeries, thereby reducing their perioperative complications and length of hospital stay. FIG. 1 depicts a percutaneous filtration catheter according to one embodiment. The catheter has elongate member 1, distal end 2, and proximal end 3. Balloon occluder 5, which may comprise an elastomeric balloon, is mounted on elongate member 1 and communicates with inflation lumen 6. Expandable filter 10 is mounted on elongate member 1 distal the balloon occluder and can be operated by actuating mechanism 12 at the proximal end of the catheter.

FIG. 2 depicts another embodiment of a percutaneous filtration catheter having a second lumen. The catheter carries second lumen 20 in addition to lumen 6 which communicates with balloon occluder 5 and inflation port 7 for inflating the balloon occluder. Second lumen 20 communicates with port 22 and can be used to infuse cardioplegia solution, aspirate fluid or air, and/or to house a pressure monitor. Filter 10, mounted on elongate member 1, has expansion frame 15 and can be actuated by mechanism 12 at proximal end 3 of the catheter.

The length of a percutaneous filtration catheter is generally between 20 and 90 centimeters, preferably approximately 50 centimeters. The outer diameter of the catheter is generally between 0.1 and 0.4 centimeters, preferably approximately 0.2 centimeters. The balloon occluder, when inflated, will generally have a diameter between 1.0 and 5.0 centimeters, more preferably between 2.0 and 4.0 centimeters. The filter, when expanded, will generally have a diameter between 1.0 and 5.0 centimeters, more preferably between 2.0 and 4.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Methods of using the devices disclosed herein are illustrated in FIG. 3. After a small percutaneous incision is made in a patient's femoral artery, distal end 2 of the percutaneous catheter is introduced through the incision and advanced into the ascending aorta. Expandable filter 10 is then expanded to entrap embolic material originating from the heart or the aorta, including air, atheromatous plague, tissue debris, fat, or thrombi. Balloon occluder 5 is inflated through its communicating inflation lumen 6 to provide aortic occlusion for cardiopulmonary bypass. Cardiac arrest can be achieved by delivering cardioplegia solution upstream to the heart through lumen 20 and port 22. Lumen 20 and port 22 can also be used to place a pressure monitor or to aspirate fluid, blood, air, tissue, or plaque debris from the heart and the aorta. A surgeon then can proceed with various cardiothoracic surgeries.

Figure 4:
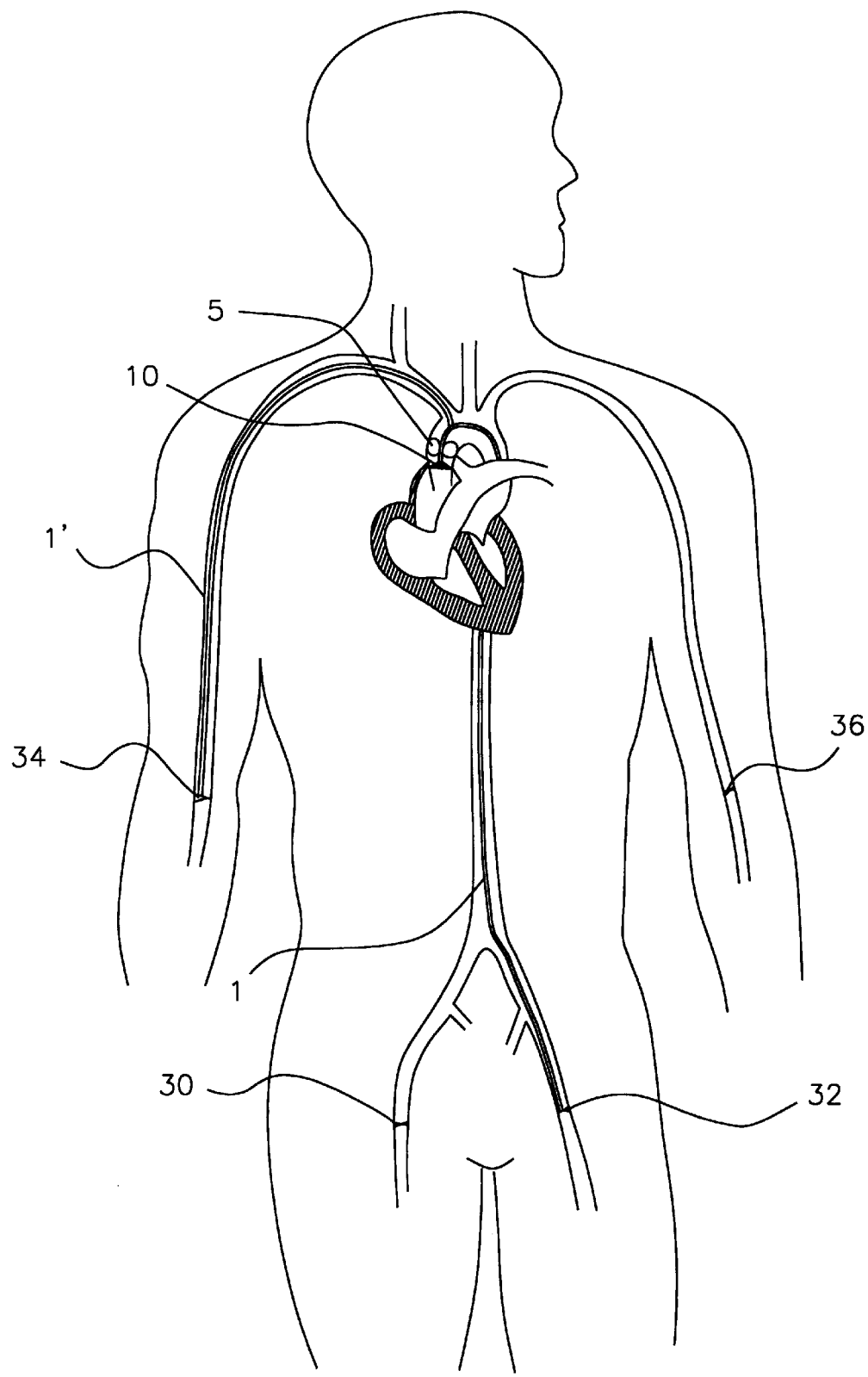
FIG. 4 depicts different access routes for entry of the percutaneous filtration catheter for use in a patient.

FIG. 4 depicts different percutaneous entry sites for a percutaneous filtration catheter. The catheter is generally inserted through a patient's femoral arteries. Right groin 30 and left groin 32 are common percutaneous incision sites for introducing elongate member 1 of the catheter, shown here entering through left groin 32 in the left femoral artery and advanced to the ascending aorta. In some patients, however, the femoral arteries are not suitable for catheter manipulation due to severe atherosclerosis. Alternatively, the catheter can be inserted through right antecubital area 34 or left antecubital area 36. Elongate member 1 of the catheter is shown inserted through antecubital area 34 and advanced through the right brachial artery and brachiocephalic trunk to enter the ascending aorta. After final placement of the catheter in the ascending aorta, expandable filter 10 is expanded to entrap emboli and balloon occluder 5 is inflated to provide circulatory isolation of the heart and coronary blood vessels from the peripheral vascular system.

It will be understood that the devices disclosed herein are particular well suited to application for valve repair surgeries because these surgeries are recognized to generate embolic material upstream of the site of aortic blockage. According to McBride et al., *Glenn's Thoracic and Cardiovascular Surgery*, $6^{th}$ Ed., Vol. 11 (1986), incorporated herein by reference, median sternotomy is often the incision used for replacing the aortic valve or any combination of valves in which the aortic valve is included. After venous cannulation of the right atrium, inferior vena cava, or superior vena cava, arterial cannulation of the aorta is established for cardiopulmonary bypass using the percutaneous filtration catheter disclosed herein. The catheter is positioned in the ascending aorta via femoral artery or brachial artery access. The balloon occluder, or other impermeable dam, is deployed to isolate the heart from peripheral circulation. The filter is deployed upstream of the occluder in order to capture calcified plaque from the aortic or mitral valve. Oxygenated blood from a bypass machine is infused through the catheter downstream of the occluder. Cardioplegia solution is administered to the aortic root while the aortic valve is manually closed by external pressure on the root of the aorta or directly into the coronary ostia.

In aortic valve repair, the aorta is opened through a transverse incision approximately 1 to 1.5 centimeters above the right coronary artery. The standard approach to mitral valve repair is often through an incision parallel to the intra-atrial groove into the left atrium. After the heavily calcific or fibrotic valve is resected sufficiently to permit visualization of the left ventricular chamber, a sponge is often placed in this cavity to enmesh any calcium that may fragment from the annulus during decalcification. A culture stick placed in the left coronary orifice prevents embolization of calcium into this vessel, and the retractor providing exposure of the valve usually blocks the right coronary orifice. A prosthetic valve is sutured into the valvular annulus after the diseased native valve is removed. The aorta is then closed with two layers of sutures. Aortic occlusion and filtration is removed, and the patient is taken off cardiopulmonary bypass.

Although the foregoing invention has, for purposes of clarity of understanding, been described in some detail by way of illustration and example, it will be obvious that certain changes and modifications may be practiced which will still fall within the scope of the appended claim.

What is claimed is:

1. A percutaneous filtration catheter, comprising:
   an elongate member having a proximal end and a distal end;
   a balloon occluder mounted on the distal end of the elongate member, the balloon defining a chamber which communicates with a lumen carried by the elongate member; and
   an expandable filter mounted on the elongate member distal the balloon occluder, the expandable filter operable independently of the balloon occluder.

2. The catheter of claim 1, wherein the balloon occluder comprises an elastomeric balloon.

3. The catheter of claim 1, further comprises a second lumen for infusion of fluid.

4. The catheter of claim 3, wherein the second lumen is adapted to receive a pressure monitor.

5. The catheter of claim 1, wherein the expandable filter is operable from the proximal end of the elongate member.

6. The catheter of claim 1, wherein the expandable filter further comprises an expansion frame.

7. The catheter of claim 6, wherein the expansion frame comprises an umbrella frame.

8. The catheter of claim 6, wherein the expansion frame comprises an inflation seal.

9. The catheter of claim 1, wherein the expandable filter is operable by manipulating at least one pull string.

10. The catheter of claim 1, wherein the expandable filter has a proximal edge bonded circumferentially and continuously to the elongate member, and a distal edge which expands radially on activation.

11. A method of percutaneous filtration for heart surgery, comprising the steps of:

provinding an elongate member having a proximal end, a distal end, a balloon occluder mounted on the distal end of the elongate member, and an expandable filter mounted on the elongate member distal the balloon occluder;

inserting the elongate member through a percutaneous incision, and advancing the distal end of the catheter into the ascending aorta;

expanding the filter;

inflating the balloon occluder; and performing surgery on the heart.

12. The method of claim 11, wherein the percutaneous incision is in a patient's femoral artery.

13. The method of claim 11, wherein the percutaneous incision is in a patient's intercostal space.

14. The method of claim 11, wherein the filter is operable from the proximal end of the elongate member.

15. The method of claim 11, wherein the surgery is heart valve repair.

16. The method of claim 11, wherein the surgery is septal defect repair.

17. The method of claim 11, wherein the expandable filter further comprises an expansion frame.

18. The method of claim 17, wherein the expansion frame comprises an umbrella frame.

19. The method of claim 17, wherein the expansion frame comprises an inflation seal.

20. The method of claim 11, wherein the expandable filter is operable by manipulating at least one pull string.

21. The method of claim 11, wherein the expandable filter has a proximal edge bonded circumferentially and continuously to the elongate member, and a distal edge which expands radially on activation.

22. The method of claim 11, wherein the step of inflating the balloon occluder is performed before the step of expanding the filter.

* * * * *